United States Patent

Kuo et al.

[11] Patent Number: 6,090,885
[45] Date of Patent: Jul. 18, 2000

[54] AMINOFUNCTIONAL SILICONE EMULSION

[75] Inventors: An-Li Kuo, Chappaqua; Virginia Van Valkenburg Powell, East Nassau; Frank J. Traver, Troy, all of N.Y.

[73] Assignee: General Electric Company, Pittsfield, Mass.

[21] Appl. No.: 09/167,122

[22] Filed: Oct. 6, 1998

[51] Int. Cl.[7] .................................................... C08L 83/08
[52] U.S. Cl. ............................ 524/838; 510/122; 524/837; 524/863; 524/864; 528/33; 528/34; 528/38
[58] Field of Search ............................... 510/122; 524/837, 524/838, 863, 864; 528/33, 34, 38

[56] References Cited

U.S. PATENT DOCUMENTS

| | | | |
|---|---|---|---|
| 4,412,035 | 10/1983 | Kurita | 524/796 |
| 4,600,436 | 7/1986 | Traver et al. | |
| 4,784,844 | 11/1988 | Thimineur et al. | |
| 5,132,443 | 7/1992 | Traver et al. | |

*Primary Examiner*—Robert Dawson
*Assistant Examiner*—Jeffrey B. Robertson

[57] ABSTRACT

A silicone emulsion useful as a component in hair care compositions In a first aspect of the present invention, a silicone emulsion comprises the product of a base catalyzed reaction of an aqueous emulsion of a hydroxy end-stopped polyorganosiloxane and an aminofunctional silane according to the structural formula:

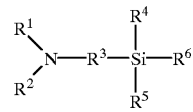

wherein:

$R^1$ and $R^2$ are each independently H, alkyl, or an aminoalkyl group according to the structural formula:

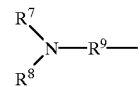

and wherein:

$R^4$, $R^5$ and $R^6$ are each independently $(C_1-C_{12})$alkyl or $(C_2-C_8)$alkoxy, provided that at least two of $R^4$, $R^5$ and $R^6$ are each $(C_2-C_8)$alkoxy;

$R^7$ and $R^8$ are each H or alkyl; and $R^3$ and $R^9$ are each independently alkylene.

13 Claims, No Drawings

AMINOFUNCTIONAL SILICONE EMULSION

FIELD OF THE INVENTION

The invention relates to silicone emulsions, more particularly to aqueous emulsions of aminofunctional silicones.

BRIEF DESCRIPTION OF THE RELATED ART

Aqueous aminofunctional silicone emulsions are known, see, for example, coassigned U.S. Pat. No. 4,600,436, which is directed to polish compositions based on such emulsions. The emulsions of the '436 patent are made by acid or base catalyzed aqueous emulsion polymerization of polyorganosiloxane monomers in the presence of one or more emulsifiers and an aminofunctional silane. The emulsions so produced typically contain methanol as a by-product of the polymerization reaction and may contain an alkoxylated alkylphenol surfactant, such as octylphenoxypolyoxyethylene.

Aminofunctional silicone emulsions have potential application in areas other than polishes, such as for example, personal care compositions and textile treatments including fiber, paper and fabric treatments. While suitable for use in applications such as polish compositions, the presence of methanol may render the emulsions disclosed in the '436 patent undesirable for use in certain applications, particularly, personal care compositions. Furthermore, the use of alkoxylated alkylphenol surfactants has recently been under scrutiny from an environmental health and safety perspective.

An aqueous aminofunctional silicone emulsion that is suitable for use as a component in personal care compositions is desired.

SUMMARY OF THE INVENTION

In a first aspect of the present invention, a silicone emulsion comprises the product of a base catalyzed reaction of an aqueous emulsion of a hydroxy end-stopped polyorganosiloxane and an aminofunctional silane of the structural formula (I):

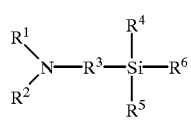

(I)

wherein:

$R^1$ and $R^2$ are each independently H, alkyl, or an aminoalkyl group according to the structural formula (II):

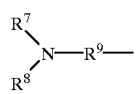

(II)

and wherein:

$R^4$, $R^5$ and $R^6$ are each independently H ($C_1$–$C_{12}$)alkyl or ($C_2$–$C_8$)alkoxy, provided that at least two of $R^4$, $R^5$ and $R^6$ are each ($C_2$–$C_8$)alkoxy;

$R^7$ and $R^8$ are each H or alkyl; and $R^3$ and $R^9$ are each independently alkylene, preferably ($C_1$–$C_{12}$)alkylene.

The aminofunctional silicone emulsion is free of polymerization reaction-generated methanol residues.

A second aspect of the present invention is directed to a hair care composition comprising the silicone emulsion disclosed above. No polymerization reaction-generated methanol residues are added to the hair care composition by addition of the aminofunctional silicone emulsion.

DETAILED DESCRIPTION OF THE INVENTION

In a preferred embodiment, the emulsion polymerization reaction mixture comprises a cationic surfactant.

In a more highly preferred embodiment, the aqueous emulsion polymerization reaction mixture comprises, based on 100 parts by weight ("pbw") of the reaction mixture, water, from 20 to 60 pbw, more preferably from 25 to 50 pbw, even more preferably from 25 to 45 pbw, of the polyorganosiloxane, from 0.05 to 0.5 pbw, more preferably from 0.1 to 0.5 pbw, of the base catalyst, from 0.1 to 12 pbw, more preferably from 1 to 10 pbw, even more preferably from 2 to 8 pbw, of the aminofunctional silane and from 1 to 20 pbw, preferably from 2 to 15 pbw, even more preferably from 2 to 10 pbw, of the cationic surfactant.

As used herein the terminology "($C_n$–$C_m$)", wherein n and m are each integers, in connection with a particular functional group means that the functional group includes from n carbon atoms to m carbon atoms per group. For example, the term "($C_1$–$C_{12}$)alkyl" means an alkyl group having from 1 to 12 carbon atoms per group, such as, for example, methyl, ethyl, isobutyl, tertbutyl, hexyl, octyl, dodecyl. ($C_2$–$C_8$)alkoxy includes, for example, ethoxy, propoxy, butoxy. ($C_1$–$C_{12}$)alkylene includes for example, methylene, ethylene, propylene, octylene, dodecylene.

In a preferred embodiment, $R^1$ and $R^2$ are each independently H or ($C_1$–$C_{12}$)alkyl, more preferably H or ($C_1$–$C_4$)alkyl, even more preferably H. In a preferred embodiment, $R^3$ is ($C_1$–$C_6$)alkylene, more preferably ethylene or propylene. In a preferred embodiment, $R^4$, $R^5$ and $R^6$ are each independently ($C_2$–$C_6$)alkoxy, more preferably ethoxy.

In a highly preferred embodiment, the aminofunctional silane comprises one or more of aminoethyldiethoxysilane, aminoethyltriethoxysilane aminopropyldiethoxysilane, aminopropyltriethoxysilane.

Suitable hydroxy end-stopped polyorganosiloxanes include linear or branched hydroxy end-stopped polyorganosiloxane homopolymers and copolymers. In a preferred embodiment, the hydroxy end-stopped polyorganosiloxane is a linear hydroxy end-stopped polyorganosiloxane made by base catalyzed aqueous emulsion polymerization of a relatively low molecular weight polyorganosiloxane. Suitable low molecular weight polyorganosiloxanes include those linear polyorganosiloxanes having a viscosity of less than or equal to about 100,000 centipoise. In a preferred embodiment, the low molecular weight polyorganosiloxane comprises one or more linear polyorganosiloxanes according to the structural formula (III):

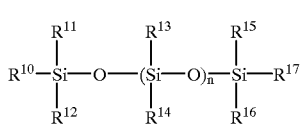

(III)

wherein:

$R^{10}$ and $R^{17}$ are each hydroxy;

$R^{11}$, $R^{12}$, $R^{13}$, $R^{14}$, $R^{15}$ and $R^{16}$ are each independently H, alkyl, more preferably ($C_1$–$C_{12}$)alkyl, alkenyl, more preferably ($C_2$–$C_{12}$)alkenyl, aryl or aralkyl; and each n is independently an integer from 100 to 6,000.

Alkenyl includes, for example,, ethenyl, propenyl, butenyl, octenyl. As used herein, the term "aryl" means a radical containing one or more aromatic rings per radical, which may optionally be substituted on the one or more aromatic rings with one or more alkyl or alkenyl groups, each preferably containing from 2 to 6 carbon atoms per group and which, in the case of two or more rings, may be fused rings, and includes for example, phenyl, naphthyl, tolyl. Aralkyl includes, for example, phenethyl.

In a more highly preferred embodiment, $R^{11}$, $R^{12}$, $R^{31}$, $R^{14}$, $R^{15}$ and $R^{16}$ are each independently $(C_1-C_{12})$alkyl, even more preferably $(C_1-C_6)$alkyl.

In a more highly preferred embodiment, each n is independently an integer from 200 to 2000, even more preferably from 300 to 1000.

In a highly preferred embodiment, the relatively low molecular weight polyorganosiloxane comprises one or more hydroxy end-stopped polydimethylsiloxanes, wherein each $R^{10}$ and $R^{17}$ are each hydroxy and $R^{11}$, $R^{12}$, $R^{13}$, $R^{14}$, $R^{15}$ and $R^{16}$ are each methyl.

Suitable low molecular weight linear polyorganosiloxanes can be formed from cyclic polyorganosiloxanes, such as for example, polyoctamethyltetrasiloxane, polydodecamethylhexasiloxane, by equilibration in an aqueous medium.

In a preferred embodiment, the polymerization of the low molecular weight polyorganosiloxane to form the aqueous emulsion of a hydroxy end-stopped polyorganosiloxane and the reaction of the hydroxy end-stopped polyorganosiloxane with the aminofunctional silane are each conducted in the presence of one or more surfactants. Suitable surfactants are those nonionic surfactants and cationic surfactants that promote dispersion of the low molecular weight polyorganosiloxane and the polyorganosiloxane polymer in the aqueous reaction medium.

Suitable cationic surfactants and include, for example, quaternary ammonium salts, including ethoxylated quaternary ammonium salts and quaternary ammonium esters. Suitable quaternary ammonium salts include, for example, dialkyldimethylammonium salts, alkyldimethylammonium salts, alkyltrimethyl ammonium salts. Suitable ethoxylated quaternary ammonium salts include, for example, N,N,N', N',N'-pentamethyl-N-tallow-1,3-propoanediammonium dichloride. Suitable quaternary ammonium esters include, for example, N,N-di(tallowyl-oxy-ethyl)-N,N-dimethyl ammonium chloride.

In a preferred embodiment the surfactant comprises a cationic surfactant selected from quaternary ammonium salts, more preferably an alkyltrimethyl ammonium salt, even more preferably a $(C_8-C_{20})$alkyltrimethyl ammonium chloride.

Suitable non-ionic surfactants include, for example, alcohol alkoxylates, ethylene-propylene oxide copolymers and alkoxylated alkylphenols. Alcohol alkoxylates and ethylene-propylene oxide copolymers are preferred, with alcohol ethoxylates being even more preferred. In a highly preferred embodiment, the nonionic surfactant exhibits an HLB value of greater than or equal to 10, more preferably from 10 to 30, most preferably from 12 to 18.

In a highly preferred embodiment, no alkoxylated alkylphenol surfactants are present the medium in which the reaction of the hydroxy end-stopped polyorganosiloxane with the aminofunctional silane is conducted, so that use of the aminofunctional silicone emulsion formed by such reaction as a component in another composition, such as a personal care composition, does not add any alkoxylated alkylphenol surfactants to such composition.

In a highly preferred embodiment, the surfactant comprises a non-ionic surfactant selected from $(C_6-C_{24})$alcohol ethoxylates containing from 5 to 30 ethylene oxide units per molecule.

In a preferred embodiment, both the cationic surfactant and a non-ionic surfactant are used.

Suitable base catalysts are well known and include, for example, strong alkalis, such as, for example, potassium hydroxide, sodium hydroxide tetraallyl ammonium hydroxide. In a preferred embodiment, potassium hydroxide is used as the base catalyst.

In a preferred embodiment, a low molecular weight polyorganosiloxane, a surfactant, and an acid or base catalyst and water are combined in a reaction vessel, homogenized and heated to form a hydroxy end-stopped polyorganosiloxane. An aminofunctional silane is then added to the reaction mixture and heated to drive condensation of the hydroxy end-stopped polyorganosiloxane and aminofunctional silane to form an aminofuntional silicone polymer. Following the condensation reaction, the catalyst is neutralized. It will be appreciated that, alternatively, the reaction can be conducted in one step by acid or base catalyzed equilibration of a cyclic polyorganosiloxane in an aqueous medium in the presence of surfactant and an aminofunctional silane.

The silicone emulsion of the present invention may be used in a variety of applications, including, for example, paper treatment, textile treatment, polishes, coatings and personal care compositions, preferably hair care compositions.

Hair care composition according to the present invention may optionally contain one or more additives known in the personal care field, such as, for example, nonreactive carrier or diluents such as, for example, water, alcohols, hydrocarbons; surfactants, which may be anionic, nonionic, amphoteric, zwitterionic or cationic surfactants such as, for example, ammonium lauryl sulfate, ammonium laureth sulfate, coamidopropyl betaine; conditioning agents such as, for example, dicetyldimonium chloride and stearamidopropyl dimethylamine; foam stabilizers such as, for example, dimethicone copolyols; foam boosters such as, for example, cocamide MEA; thickeners, such as, for example, glyceryl stearate, cetearyl alcohol, cetyl alcohol; humectants such as, for example, glycerin; preservatives such as, for example, methylparaben, propylparaben and pH adjusters such as, for example, citric acid.

In a first preferred embodiment, the hair care composition is a hair conditioner composition, comprising the silicone emulsion of the present invention and, preferably, a diluent, such as for example, water. More preferably, the condition further comprises a second conditioner in addition to the silicone emulsion, and even more preferably, still further comprises a thickener.

In a second preferred embodiment, the hair care composition is a hair conditioning shampoo composition, comprising the silicone emulsion of the present invention, one or more surfactants and, preferably, a diluent, such as, for example, water.

The silicone emulsion of the present invention is effective in imparting improved hair conditioning properties to hair care compositions, without adding methanol residues to such compositions and, in a preferred embodiment, without adding alkoxylated phenol surfactants to such compositions.

EXAMPLE 1

A silicone emulsion according to the present invention was made as follows. A siloxane (525 pbw of a mixture 70% linear hydroxy-stopped polydimethylsiloxane having from about 50 to about 100 siloxane structural units per molecule and about 30 wt % cyclic polyorganosiloxanes (predominantly polyoctamethyltetrasiloxane), a cationic surfactant (60 pbw of a 25% aqueous solution of cetyltrimethyl ammonium chloride), a non-ionic surfactant (90 pbw of a ($C_{11}$–$C_{14}$)isoalcohol ethoxylate (Renex 30, ICI) a base (7.5 pbw of a 45% aqueous solution of KOH) and water (683 pbw deionized water) were combined in a stainless steel reaction vessel, mixed and then homogenized in a AVP Gaulin homogenizer at a pressure of 6000 pounds per square inch, heated to 73° C. and then maintained at that temperature for about five hours to form a hydroxy end-stopped polydimethylsiloxane emulsion (38% solids, 114 nm particle size). The temperature of the emulsion was then reduced to less than 40° C. and then 63 pbw aminopropyltriethoxysilane was added to the emulsion. The combined hydroxy end-stopped polydimethylsiloxane emulsion and silane mixture was then heated to 45° C. and maintained at that temperature for about one hour to form an aqueous aminofunctional silicone polymer emulsion. The aminofunctional silicone polymer emulsion was then neutralized with acetic acid to a pH of about 11 and 0.1% by weight of the emulsion of a biocide (1,2-benzisothiazoline, Proxel GXL, Zeneca) was added to the emulsion. The solids content of the aqueous aminofunctional silicone emulsion was found to be about 40%, with an amine equivalent of about 0.3 milliequivalents per gram.

EXAMPLE 2

A hair conditioner composition according to the present invention is made as follows. A premix A is made by combining 86.85 pbw water, 0.50 pbw hydroxyethylcellulose, 2.00 pbw glycerin, 0.20 pbw methylparaben and 0.10 pbw methylparaben and heating the combined ingredients to 65° C. A premix B is made by combining and melting 3.00 pbw of a mixture of cetearyl alcohol, dicetyldimonium chloride and stearylamidopropyl dimethylamine, 0.80 pbw glyceryl stearate and 1.50 pbw cetyl alcohol. Molten premix B is added to premix A, the resultant mixture is cooled to 40° C. and then 0.05 pbw of a mixture of methylchloroisothiazolinone and methylisothiazolinone and 5.00 pbw of the silicone emulsion made according the process disclosed above in Example 1 are added to the cooled mixture. The pH of the resultant mixture is then adjusted to 4.5 by adding citric acid.

The hair conditioner composition of Example 2 provides improved combability, softness, body and volume when applied to hair.

EXAMPLE 3

A conditioning shampoo composition according to the present invention is made as follows. A premix C is made by combining 38.72 deionized water, 1.00 pbw dimethicone copolyol, 24.00 pbw of a 26% aqueous solution of ammonium lauryl sulfate, 14.30 pbw of a 28% aqueous solution of ammonium laureth sulfate and 1.43 pbw cocamidopropyl betaine and heating the combined ingredients to 65° C. A premix D is made by combining and melting 4.00 pbw cocamide MEA and 1.5 pbw PEG-150 pentaerythriyl tetrastearate. Molten premix D is added to premix C, the resultant mixture is cooled to 40° C. and then 0.05 pbw a mixture of a mixture of methylchloroisothiazolinone and methylisothiazolinone and 5.0 pbw of the silicone emulsion made according the process disclosed above in Example 1 are then added. The pH of the resultant mixture is then adjusted to within the range of 6.0–6.5 by adding citric acid.

The conditioning shampoo composition of Example 3 provides improved combability, softness, body and volume when applied to hair.

EXAMPLE 4

A water-in-oil hair conditioner according to the present invention is made as follows. An oil phase premix is made by combining 10 pbw of a cyclopentasiloxane/dimethicone copolyol, and 5 pbw amino silicone emulsion according to Example 1. A water phase premix is made by combining 0.2 pbw sodium chloride with 84.8 pbw water. 85 pbw of the water phase premix is slowly added to the oil phase, with good mixing, and then 0.05 pbw of a mixture of methylchloroisothiazolinone and methylisothiazolinone is added to the combined premixes.

The hair conditioner composition of example 4 provides improved wet combing, soft and silky wet feel, dry combing, soft, silky and light dry feel, improved fly-away and manageability, when applied to hair.

What is claimed is:

1. A silicone emulsion, comprising the product of a base catalyzed reaction of an aqueous emulsion of a hydroxy end-stopped polyorganosiloxane and an aminofunctional silane of the structural formula:

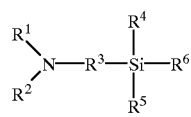

wherein:

$R^1$ and $R^2$ are each independently H, alkyl, or an aminoalkyl group according to the structural formula:

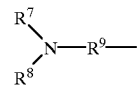

and wherein:

$R^4$, $R^5$ and $R^6$ are each independently H, ($C_1$–$C_{12}$)alkyl or ($C_2$–$C_8$alkoxy, provided that at least two of $R^4$, $R^5$ and $R^6$ are each ($C_2$–$C_8$)alkoxy;

$R^7$ and $R^8$ are each H or alkyl; and $R^3$ and $R^9$ are each independently alkylene.

2. The composition of claim 1, wherein the emulsion polymerization reaction mixture comprises a cationic surfactant.

3. The composition of claim 1, wherein the emulsion polymerization reaction mixture comprises, based on 100 parts by weight of the mixture, water, from 20 to 60 parts by weight of the polyorganosiloxane, from 0.05 to 0.5 parts by weight of the base catalyst, from 0.1 to 12 parts by weight, of the aminofunctional silane and from 1 to 20 parts by weight of the cationic surfactant.

4. The composition of claim 1, wherein $R^1$ and $R^2$ are each independently H or ($C_1$–$C_{12}$)alkyl and $R^3$ is ($C_1$–$C_6$) alkylene.

5. The composition of claim 1, wherein $R^4$, $R^5$ and $R^6$ are each independently H or ($C_2$–$C_6$)alkoxy.

6. The composition of claim 1, wherein the aminofunctional silane comprises one or more of aminoethyldiethoxysilane aminoethyltriethoxysilane, aminopropyldiethoxysilane, aminopropyltriethoxysilane.

7. The composition of claim 1, wherein the polyorganosiloxane comprises one or more linear polyorganosiloxanes according to the structural formula:

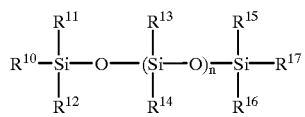

wherein $R^{10}$ and $R^{17}$ are each hydroxy, $R^{11}$, $R^{12}$, $R^{13}$, $R^{14}$, $R^{15}$ and $R^{16}$ are each independently H, alkyl, alkenyl, aryl or aralkyl; and each n is independently an integer from 100 to 6,000.

8. The composition of claim 7, wherein the polyorganosiloxane comprises one or more hydroxy end-stopped polydimethylsiloxanes, wherein $R^{10}$ and $R^{17}$ are each hydroxy and $R^{11}$, $R^{12}$, $R^{13}$, $R^{14}$ $R^{15}$ and $R^{16}$ are each methyl.

9. The composition of claim 1, wherein the polyorganosiloxane is formed by equilibration of cyclic polyorganosiloxanes in an aqueous emulsion polymerization reaction mixture.

10. The composition of claim 1, wherein emulsion polymerization reaction mixture further comprises a nonionic surfactant selected from alcohol alkoxylates and ethylene-propylene oxide copolymers.

11. A hair care composition, comprising the silicone emulsion of claim 1.

12. The hair care composition of claim 11, wherein the hair care composition is a hair conditioner.

13. The hair care composition of claim 11, wherein the hair care composition is a hair conditioning shampoo.

* * * * *